(12) United States Patent
Sun et al.

(10) Patent No.: US 8,426,660 B2
(45) Date of Patent: Apr. 23, 2013

(54) PROCESS FOR PURIFICATION OF ETHYLENE-CONTAINING FEEDSTREAMS

(75) Inventors: Mingyong Sun, Louisville, KY (US);
Martin Byran, Prospect, KY (US);
Steven A. Blankenship, Radcliff, KY (US); Michael A. Urbancic, Louisville, KY (US)

(73) Assignee: Sud-Chemie Inc., Louisville, KS (US)

( * ) Notice: Subject to any disclaimer, the term of this patent is extended or adjusted under 35 U.S.C. 154(b) by 1108 days.

(21) Appl. No.: 12/195,678

(22) Filed: Aug. 21, 2008

(65) Prior Publication Data
US 2010/0048972 A1    Feb. 25, 2010

(51) Int. Cl.
*C07C 5/08*    (2006.01)

(52) U.S. Cl.
USPC ............ 585/259; 585/258; 585/262; 585/261

(58) Field of Classification Search .................. 585/257, 585/258, 259
See application file for complete search history.

(56) References Cited

U.S. PATENT DOCUMENTS

| | | | |
|---|---|---|---|
| 1,418,246 A | 5/1922 | Frazer et al. | |
| 2,475,155 A | 7/1949 | Rosenblatt | |
| 2,747,970 A | 10/1951 | Rosenblatt | |
| 3,084,023 A * | 4/1963 | Andersen et al. | 423/239.1 |
| 3,305,597 A | 2/1967 | Straschil et al. | |
| 3,489,809 A * | 1/1970 | Romeo, Sr. et al. | 585/260 |
| 4,299,800 A | 11/1981 | Nishikawa et al. | |
| 4,430,253 A * | 2/1984 | Dubeck et al. | 502/185 |
| 4,581,343 A | 4/1986 | Blanchard et al. | |
| 4,705,906 A * | 11/1987 | Brophy et al. | 585/262 |
| 5,227,145 A | 7/1993 | Kintaichi et al. | |
| 5,414,170 A * | 5/1995 | McCue et al. | 585/264 |
| 5,981,818 A | 11/1999 | Purvis et al. | |
| 6,080,905 A | 6/2000 | Kaminsky et al. | |
| 6,124,517 A | 9/2000 | Kaminsky et al. | |
| 6,197,721 B1 * | 3/2001 | Didillon et al. | 502/326 |
| 6,388,149 B2 | 5/2002 | Rühl et al. | |
| 6,395,952 B1 | 5/2002 | Barchas | |
| 6,429,167 B1 | 8/2002 | Maeno et al. | |
| 6,936,568 B2 * | 8/2005 | Blankenship et al. | 502/330 |
| 7,144,566 B2 | 12/2006 | Anzai et al. | |
| 7,169,954 B2 | 1/2007 | Mizuno et al. | |
| 7,220,700 B2 * | 5/2007 | Lowe et al. | 502/325 |
| 8,309,776 B2 * | 11/2012 | van Egmond et al. | 585/261 |
| 2005/0096217 A1 * | 5/2005 | Rokicki et al. | 502/327 |

OTHER PUBLICATIONS

International Search Report for PCT/US2009/054592, Mar. 31, 2010, WIPO.
Written Opinion of the International Search Authority for PCT/US2009/054592, Mar. 31, 2010, WIPO.

* cited by examiner

*Primary Examiner* — Tam M Nguyen
(74) *Attorney, Agent, or Firm* — RatnerPrestia

(57) ABSTRACT

A method for purification of ethylene-containing feedstreams from steam crackers or fluid catalytic crackers (FCC), wherein the feedstreams further comprises hydrogen, carbon monoxide, acetylenes, oxygen, nitric oxides, is disclosed. The method comprises contacting an ethylene-comprising gas stream with a Ru-based catalyst at reaction temperatures of at least 120°C. The process results in an ethylene-containing feedstream wherein the ethylene is essentially free of acetylenes, nitric oxides and oxygen. The purifying of the feedstream occurs with minimal loss of ethylene.

22 Claims, No Drawings

PROCESS FOR PURIFICATION OF ETHYLENE-CONTAINING FEEDSTREAMS

BACKGROUND

The present development is a method that can be useful in purification of raw gas or offgas streams from steam crackers or fluid catalytic crackers (FCC). By the method of the present development, acetylene, methylacetylene, NO, and $O_2$ are simultaneously removed from a raw gas feedstream that comprises ethylene, hydrogen, and CO without significant loss of ethylene, using a supported Ru-based catalyst. The catalyst comprises between 0.01 wt % to 5 wt % ruthenium distributed on a support selected from alumina or other commonly known catalyst support materials.

Catalytic cracking processes, such as fluid catalytic cracking (FCC) and deep catalytic cracking (DCC), have been widely used in industry for many years to produce transportation fuels, such as gasoline and diesel. The off-gases from the FCC and DCC processes contain valuable products such as ethylene and propylene. However, these off-gas streams contain relatively dilute concentrations of olefins and it is generally perceived as not being economically feasible to recover the olefins by conventional means, such as fractionation. Thus, most refineries use the off-gas as fuel-gas.

Recently, the recovery of these relatively high value olefins from off gas streams has gained increasing interest. For example, U.S. Pat. No. 5,981,818 describes a process for recovery of dilute olefins from off-gases. Besides valuable olefins, FCC/DCC off-gases also contain detrimental impurities such as acetylenes and di-olefins. These impurities need to be removed from the off-gas streams in order to utilize the high value olefins in downstream processes. Typically, acetylenes and dienes found in olefin streams are commercially removed by a selective hydrogenation process.

Most selective acetylene hydrogenation operations at the commercial scale use Pd-based catalysts. In addition to hydrocarbons, an off-gas stream often contains nitric oxides, oxygen, sulfur, and other impurities. The Pd-based catalysts have high activity and selectivity for selective hydrogenation of acetylene and dienes; but they are very sensitive to sulfur and some other poisons. Moreover, the Pd-based catalysts are not known to be particularly effective for removal of nitric oxides and/or oxygen.

Nickel catalysts have also been used in selective hydrogenation of acetylene and dienes. Nickel catalysts are resistant to sulfur poisoning, but are not selective toward hydrogenation of acetylene. Most commonly, while acetylene is removed, significant amounts of olefins are also hydrogenated to saturated hydrocarbons. Nickel-based catalysts also tend to form nickel carbonyl when the carbon monoxide level is high in the feed gas stream, particularly at low temperatures. Nickel carbonyl is a highly volatile, highly toxic substance which can deposit in downstream equipment and pose a significant safety hazard to workers in the area.

U.S. Pat. No. 2,747,970 teaches and claims a process of removing carbon monoxide and carbon dioxide from a gas stream using a catalyst consisting of 0.01% to 2.0% ruthenium on an activated earth metal oxide, such as activated alumina. The process comprises directly contacting the gas stream with the supported catalyst while maintaining a reaction temperature of at least 120° C. until the carbon content of the CO and $CO_2$ is substantially completely converted to methane. However, the process does not teach that the same catalyst and method can be used to remove acetylene, methylacetylene, butadiene, NO, and $O_2$ from an ethylene gas stream without risk of loss of ethylene. The prior art which does teach the use of ruthenium catalysts for purification of ethylene streams typically cites the ruthenium catalysts as examples of ineffective catalysts for such applications. For example, in U.S. Pat. No. 4,299,800, a catalyst comprising 0.5 wt % ruthenium on alumina was evaluated for oxygen removal from an ethylene comprising feedstream. At low temperatures (50° C.), oxygen removal was low and ethylene conversion was essentially non-detectable. However, at higher temperatures (200° C.), oxygen removal reached 99.4%, but with concomitant ethylene conversion (loss) of 11.2%, as compared to less than 5% ethylene conversion when using silver, gold or vanadium on alumina.

Thus, there is a need for a process for removing oxygen, acetylenes, and nitric oxides from off gas streams wherein the ethylene is not converted to lower value hydrocarbons during the purification process and wherein the purified ethylene-containing gas stream comprises less than about 1 ppm of each of acetylenes, nitric oxides and oxygen.

SUMMARY OF THE PRESENT INVENTION

The present development is a method for purification of ethylene-containing feedstreams from steam crackers or fluid catalytic crackers (FCC), wherein the feedstreams further comprise hydrogen, carbon monoxide, oxygen, and acetylenes. The method comprises contacting an ethylene-comprising gas stream with a Ru-based catalyst. The process results in an ethylene-containing product stream comprising less than about 1 ppm acetylenes, less than about 1 ppm nitric oxides and less than about 1 ppm oxygen. The purifying of the feedstream occurs with minimal loss of ethylene.

DETAILED DESCRIPTION OF THE INVENTION

The present development is a method for removing oxygen, acetylenes, and nitric oxides from ethylene-containing feedstreams which further comprise hydrogen, carbon monoxide, acetylenes, and oxygen. The method comprises contacting an ethylene-comprising gas stream with a Ru-based catalyst comprising between 0.01 wt % to 5 wt % ruthenium distributed on a carrier.

The ethylene-containing feedstream may be the off-gas stream from any steam cracker or fluid catalytic cracker. Typically, the gas stream will comprise hydrogen gas, carbon monoxide, oxygen, nitrogen oxides, ethane, ethylene and acetylene.

The ruthenium-based catalyst may be any catalyst comprising ruthenium distributed on a typical catalyst support material, such as, without limitation, alumina, titania, zirconia, silica, metal aluminates, and combinations thereof. Methods of preparing supported ruthenium catalysts are well-known in the art. Optionally, the catalyst may further include promoters, such as, without limitation, silver, gold, copper, zinc, bismuth, lead or combinations thereof. In an exemplary embodiment, the catalyst comprises ruthenium distributed on an alumina support wherein the ruthenium is distributed on the support by impregnating an alumina support with a ruthenium salt solution. In an alternative exemplary embodiment, the catalyst comprises ruthenium distributed on an alumina support wherein the support has a BET surface area of at least than 3 $m^2/g$, and preferably has a BET surface area of from about 3 $m^2/g$ to about 200 $m^2/g$. In a second alternative exemplary embodiment, the catalyst comprises ruthenium distributed on an alumina support wherein the ruthenium is distributed on the support by impregnating an alumina support with a ruthenium salt solution in such a manner as to remain on the outer layer of the support. In a preferred embodiment, the catalyst comprises between 0.01 wt % to 1 wt % ruthenium distributed on the outer layer of an alumina carrier having a BET surface area from about 3 m$^2$/g to about 200 m$^2$/g, wherein "distributed on the outer layer" of the support means that the ruthenium is located within 300 μm of an exterior surface of the support.

The process comprises directly contacting the gas stream with the supported catalyst while maintaining a reaction temperature of at least 120° C. until the acetylene content decreases to less than one (1) ppm and the nitric oxide content decreases to less than one (1) ppm and the oxygen content decreases to less than one (1) ppm.

As representative examples, several catalysts were acquired and evaluated for removal of impurities from an ethylene feedstream. These examples are presented to further explain the invention and are not intended, or to be taken, to limit the scope of the invention.

Catalyst samples evaluated:

Catalyst 1: Commercial Pd-based catalyst, OleMax 250; obtained from Süd-Chemie Inc., Louisville, Ky.

Catalyst 2: 0.15% ruthenium on a low surface area (3.6 m$^2$/g) alumina carrier;

The catalyst may be reduced or sulfided before use. The catalyst is reduced after being loaded into the reactor and before introduction of the ethylene-containing gas stream by feeding hydrogen or a hydrogen-containing gas through the catalyst a temperature of at least 100° C. for at least one minute. The catalyst is sulfided after being loaded into the reactor and before introduction of the ethylene-containing gas stream by feeding a sulfur-containing gas stream through the catalyst at a temperature of at least 150° C. for at least one minute.

Catalysts 1-4 are tested in the continuous flow reactor. Approximately 50 cc of catalyst is loaded into the reactor, the reactor temperature is adjusted to a predetermined temperature (as indicated in Table 1), and an ethylene-containing feedstream contaminated with oxygen, acetylene, and nitric oxide is fed through the reactor at a gas hourly space velocity of 2500 hr$^{-1}$ while the pressure is held at 1.9 MPa. Gas samples from an inlet and outlet reactor are analyzed using an on-line gas chromatograph and the findings are summarized in Table 1.

TABLE 1

| | Catalyst 1 | | Catalyst 2 | | Catalyst 3 | | Catalyst 4 | |
|---|---|---|---|---|---|---|---|---|
| | Catalyst | | | | | | | |
| | Pd/Al$_2$O$_3$ | | Ru/Al$_2$O$_3$ (low SA) | | Ru/Al$_2$O$_3$ (med SA) | | Ru/Al$_2$O$_3$ (high SA) | |
| | Reactor Temp | | | | | | | |
| | 97.1° C. | | 200° C. | | 217° C. | | 197° C. | |
| Gas Composition | Feed | Product | Feed | Product | Feed | Product | Feed | Product |
| C$_2$H$_4$ (%) | 23.3 | 21.6 | 22.6 | 22.2 | 22.1 | 21.6 | 22.2 | 22.0 |
| H$_2$ (%) | 9.6 | 7.68 | 9.1 | 8.6 | 8.7 | 8.3 | 8.5 | 8.1 |
| C$_2$H$_2$ (ppm) | 406 | 0.4 | 680 | <0.5 | 656 | <0.5 | 668 | <0.5 |
| NO (ppm) | 0.413 | <0.010 | 0.62 | 0.01 | 0.707 | 0.015 | 0.584 | 0.017 |
| O$_2$ (ppm) | 3663 | 3561 | 2891 | 0.37 | 2787 | 0.54 | 2792 | 0.32 |
| CO (%) | 0.59 | 0.50 | 2.18 | 1.88 | 2.38 | 2.09 | 2.32 | 1.99 |
| C$_2$H$_6$ (ppm) | 60 | 27270 | 37 | 2638 | 34 | 1821 | 36 | 3197 |

Catalyst 3: 0.15% ruthenium on a medium surface area (37 m$^2$/g) alumina carrier;

Catalyst 4: 0.15% ruthenium on a high surface area (165 m$^2$/g) alumina carrier;

Catalyst 5: 0.30% ruthenium on a high surface area (165 m$^2$/g) alumina carrier;

Catalyst samples evaluations:

The prepared catalysts are tested in a continuous flow reactor by loading approximately 50 cc of catalyst into the reactor and then feeding a contaminated ethylene-containing feedstream through the loaded catalyst. For testing purposes, in general, the reactor temperature is adjusted to a temperature of from about 120° C. to about 300° C., the carbon monoxide content is held between about 0.05% and 5%, and the sulfur content is held below about 50 ppm. The hydrogen partial pressure is held between about 0.05 MPa and 2 MPa with a gas hourly space velocity of from about 500 hr$^{-1}$ to 10,000 hr$^{-1}$; more preferably, the hydrogen partial pressure is held between about 0.10 MPa and 1 MPa with a gas hourly space velocity of from about 1000 hr$^{-1}$ to 5,000 hr$^{-1}$; and most preferably, the hydrogen partial pressure is held between about 0.10 MPa and 0.3 MPa with a gas hourly space velocity of from about 1500 hr$^{-1}$ to 3500 hr$^{-1}$ and with a hydrogen concentration of from about 5% to about 15%.

As indicated in Table 1, the palladium catalyst and the ruthenium catalysts all effectively retain ethylene and hydrogen in the gas stream, although the ruthenium catalysts retain a higher relative percentage of these gases than is observed with the palladium catalyst. Further, the palladium catalyst and the ruthenium catalysts all effectively reduce the levels of acetylene and nitrogen oxides present in the feed stream. However, the ruthenium catalysts are significantly more effective at removing oxygen from the feedstream than the palladium catalyst. Also, most likely because the ruthenium catalysts are less active for hydrogenation of ethylene than the palladium catalyst, less ethane is produced when the ethylene-containing feedstream contacts the ruthenium catalysts than when the feedstream contacts the palladium catalyst.

Catalyst 5 is tested in the continuous flow reactor at various reactor temperatures, and with additional carbon monoxide or hydrogen sulfide in the feedstream. Approximately 50 cc of catalyst is loaded into the reactor, the reactor temperature is adjusted to a predetermined temperature (as indicated in Table 2), and an ethylene-containing feedstream contaminated with oxygen, acetylene and optionally, nitric oxide or carbon monoxide or hydrogen sulfide, is fed through the reactor at a gas hourly space velocity of 2500 hr$^{-1}$ while the pressure is held at 1.9 MPa. Gas samples from an inlet and outlet reactor are analyzed using an on-line gas chromatograph and the findings are summarized in Table 2.

TABLE 2

| | Catalyst Ru/Al$_2$O$_3$ (high SA) Variable | | | | | | | | | |
|---|---|---|---|---|---|---|---|---|---|---|
| | Temperature | | | CO Addition React Temp | | | H$_2$S Addition | | | |
| | | 139° C. | 154° C. | | 162° C. | 176° C. | | 186° C. | | |
| Gas Comp | Feed | Product | Product | Feed | Product | Product | Feed | Product | Product | Product |
| C$_2$H$_4$ (%) | 24.08 | 22.33 | 22.52 | 23.68 | 23.44 | 23.38 | 23.68 | 22.24 | 23.39 | 21.8 |
| H$_2$ (%) | 10.21 | 9.89 | 9.70 | 10.5 | 9.7 | 9.6 | 10.5 | 9.7 | 9.7 | 10.7 |
| CO (%) | 1.1 | 0.79 | 0.73 | 2.39 | 2.11 | 2.11 | 2.39 | 2.13 | 2.03 | 2.06 |
| H$_2$S (ppm) | — | — | — | — | — | — | — | 0 | 8 | 18 |
| C$_2$H$_2$ (ppm) | 469 | 2.5 | 0.4 | 501 | <0.5 | <0.5 | 501 | <0.5 | <0.5 | <0.5 |
| NO (ppm) | 0.5 | 0.016 | 0.008 | 0.959 | 0.020 | 0.023 | 0.959 | 0.013 | 0.017 | 0.017 |
| O$_2$ (ppm) | 2869 | 113 | 0.85 | 3181 | 43 | 0.54 | 3181 | 0.1 | 0.2 | 1.4 |
| C$_2$H$_6$ (ppm) | 21 | 1610 | 3850 | 17 | 1162 | 2742 | 17 | 2888 | 1440 | 830 |

As indicated in Table 2, even under adverse conditions, the ruthenium catalyst effectively retains ethylene and hydrogen in the gas stream. Further, the ruthenium catalyst effectively reduces the levels of acetylene and oxygen present in the feed stream, and produces relatively low quantities of ethane.

Thus, by contacting an ethylene-containing feedstream which further comprises hydrogen, carbon monoxide, oxygen, acetylene, and nitric oxide with a supported ruthenium catalyst, wherein the catalyst comprises between 0.01 wt % to 5 wt % ruthenium, in a continuous flow reactor with the catalyst held at a temperature of at least about 120° C., acetylenes, nitric oxides and oxygen can be removed from the gas stream with a minimal loss of ethylene.

It is understood that one skilled in the art may make alterations to the embodiments shown and described herein without departing from the scope of the invention. For example, it is anticipated that the reactor pressure and the gas hourly flow rate may be adjusted by those skilled in the art to accommodate different sized reactors.

What is claimed is:

1. A method for purifying ethylene from an ethylene-comprising gas stream which further comprises acetylenes, 5% to 15% hydrogen, oxygen and nitric oxide, the method comprising contacting the ethylene-comprising gas stream with a supported ruthenium catalyst comprising between 0.01 wt % to 5 wt % ruthenium to effect hydrogenation of the acetylenes until the gas stream comprises less than about 1 ppm acetylenes and less than about 1 ppm nitric oxides and less than about 1 ppm oxygen.

2. The method of claim 1 wherein the supported ruthenium catalyst is heated to a temperature of at least about 120° C. before making contact with the gas stream.

3. The method of claim 1 wherein the gas stream is contacted with the catalyst in a continuous flow reactor.

4. The method of claim 3 wherein the reactor is maintained at a temperature of from 120° C. to 300° C.

5. The method of claim 3 wherein the reactor has a hydrogen partial pressure of between 0.05 MPa and 2 MPa.

6. The method of claim 1 wherein the gas stream has a gas hourly space velocity of 500 hr$^{-1}$ to 10,000 hr$^{-1}$.

7. The method of claim 5 wherein the reactor has a hydrogen partial pressure of between 0.10 MPa and 1 MPa.

8. The method of claim 6 wherein the gas stream has a gas hourly space velocity of 1000 hr$^{-1}$ to 5000 hr$^{-1}$.

9. The method of claim 1 wherein the ruthenium is supported on a carrier selected from the group consisting of alumina, titania, zirconia, silica, metal aluminates, and combinations thereof.

10. The method of claim 1 wherein the supported ruthenium catalysts further comprises a promoter.

11. The method of claim 10 wherein the promoter is selected from the group consisting of silver, gold, copper, zinc, bismuth, lead or combinations thereof.

12. The method of claim 1 wherein the supported ruthenium catalyst is reduced.

13. The method of claim 1 wherein the supported ruthenium catalyst is sulfided.

14. A method for purifying ethylene from an ethylene-comprising gas stream which further comprises acetylenes, hydrogen, oxygen and nitric oxide, the method comprising:
   (a) loading a continuous flow reactor with a supported ruthenium catalyst, wherein the catalyst comprises between 0.01 wt % to 5 wt % ruthenium;
   (b) heating the catalyst to a temperature of at least 120° C. in the reactor;
   (c) feeding the ethylene-comprising gas stream into the reactor under a hydrogen partial pressure of between 0.05 MPa and 2 MPa such that the gas stream is in contact with the catalyst; and
   (d) removing the ethylene-comprising gas stream from contact with the catalyst when the gas stream comprises less than about 1 ppm acetylenes and less than about 1 ppm nitric oxides and less than about 1 ppm oxygen.

15. The method of claim 14 wherein the reactor is maintained at a temperature of from 120° C. to 300° C.

16. The method of claim 14 wherein the gas stream has a gas hourly space velocity of 500 hr$^{-1}$ to 10,000 hr$^{-1}$.

17. The method of claim 14 wherein the ruthenium is supported on a carrier selected from the group consisting of alumina, titania, zirconia, silica, metal aluminates, and combinations thereof.

18. The method of claim 14 wherein the supported ruthenium catalyst further comprises a promoter selected from the group consisting of silver, gold, copper, zinc, bismuth, lead or combinations thereof.

19. The method of claim 14 wherein after step (a) and before step (c) the catalyst is reduced, while in the reactor, in hydrogen or in a hydrogen-containing gas at a temperature of at least 100° C. for at least one minute.

20. The method of claim 14 wherein after step (a) and before step (c) the catalyst is sulfided, while in the reactor, in a sulfur-containing gas stream at a temperature of at least 150° C. for at least one minute.

21. The method of claim 14, wherein ethylene-comprising gas stream further comprises 5% to 15% by weight of hydrogen.

22. The method of claim 14, wherein the contact of the ethylene-comprising gas stream with the catalyst in (c) effects a catalytic hydrogenation of the acetylenes in the gas stream.

* * * * *